(12) United States Patent
Kalvins et al.

(10) Patent No.: US 9,278,907 B2
(45) Date of Patent: Mar. 8, 2016

(54) USE OF 4-[ETHYL(DIMETHYL) AMMONIO]BUTANOATE IN THE TREATMENT OF CARDIOVASCULAR DISEASE

(75) Inventors: Ivars Kalvins, Riga (LV); Maija Dambrova, Riga (LV); Edgars Liepins, Riga (LV); Osvalds Pugovics, Riga (LV); Reinis Vilskersts, Baldone (LV); Janis Kuka, Jelgava (LV); Solveiga Grinberga, Salaspils (LV); Einars Loza, Jurmala (LV)

(73) Assignee: JSC GRINDEKS, Riga (LV)

( * ) Notice: Subject to any disclaimer, the term of this patent is extended or adjusted under 35 U.S.C. 154(b) by 833 days.

(21) Appl. No.: 13/503,144

(22) PCT Filed: Oct. 22, 2010

(86) PCT No.: PCT/EP2010/065924
§ 371 (c)(1),
(2), (4) Date: May 15, 2012

(87) PCT Pub. No.: WO2011/048201
PCT Pub. Date: Apr. 28, 2011

(65) Prior Publication Data
US 2012/0220656 A1 Aug. 30, 2012

(30) Foreign Application Priority Data
Oct. 22, 2009 (LV) ..................... P-09-181

(51) Int. Cl.
C07C 229/12 (2006.01)

(52) U.S. Cl.
CPC ..................... C07C 229/12 (2013.01)

(58) Field of Classification Search
None
See application file for complete search history.

(56) References Cited

U.S. PATENT DOCUMENTS

| 5,017,611 A * | 5/1991 | Bremanis et al. ............. 514/551 |
| 5,965,615 A | 10/1999 | Kalvinsh et al. |
| 8,940,793 B2 * | 1/2015 | Kalvins et al. ................ 514/556 |

FOREIGN PATENT DOCUMENTS

WO    WO 97/06794    2/1997

OTHER PUBLICATIONS

STN Registry No. 407-64-7. "Gamma-Butyrobetaine". STN Registry File. Retrieved Jan. 15, 2015. One Page.*
International Search Report for PCT/EP2010/065924 of Feb. 7, 2010.

* cited by examiner

*Primary Examiner* — Leslie A. Royds Draper
(74) *Attorney, Agent, or Firm* — Hueschen and Sage

(57) ABSTRACT

New compound 4-[ethyl(dimethyl)ammonio]butanoate, method of preparation thereof and use in the treatment of cardiovascular disease.

4 Claims, No Drawings

USE OF 4-[ETHYL(DIMETHYL) AMMONIO]BUTANOATE IN THE TREATMENT OF CARDIOVASCULAR DISEASE

TECHNICAL FIELD

The present invention relates to new compound 4-[ethyl (dimethyl)ammonio]butanoate, and to a method of preparation thereof (compound of formula 5)

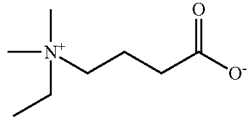

The present invention relates also to use of 4-[ethyl(dimethyl)ammonio] butanoate in the treatment of cardiovascular disease.

BACKGROUND ART

Cardiovascular diseases (CVDs) are a group of disorders of the heart and blood vesels.

An estimated 16.7 million—or 29.2% of total global deaths—result from the various forms of cardiovascular disease (CVD).

Myocardial infarction (heart attack) is a serious result of coronary artery disease. Myocardial infarction (MI) is the irreversible necrosis of heart muscle secondary to prolonged ischemia. A heart attack or myocardial infarction is a medical emergency in which the supply of blood to the heart is suddenly and severely reduced or cut off, causing the muscle to die from lack of oxygen. More than 1.1 million people experience a heart attack (myocardial infarction) each year, and for many of them, the heart attack is their first symptom of coronary artery disease. A heart attack may be severe enough to cause death or it may be silent. As many as one out of every five people have only mild symptoms or none at all, and the heart attack may only be discovered by routine electrocardiography done some time later.

A heart attack (myocardial infarction) is usually caused by a blood clot that blocks an artery of the heart. The artery has often already been narrowed by fatty deposits on its walls. These deposits can tear or break open, reducing the flow of blood and releasing substances that make the platelets of the blood sticky and more likely to form clots. Sometimes a clot forms inside the heart itself, then breaks away and gets stuck in an artery that feeds the heart. A spasm in one of these arteries causes the blood flow to stop.

γ-Butyrobetaine, from which the mammalian organism synthesises carnitine, was primarily characterised as a toxic substance which accelerates respiration, causes salivation and lacrimation, pupil dilation, vasoconstriction and heart stop in diastole LINNEWEH, W. Gamma-Butyrobetain, Crotonbetain und Carnitin im tierischen Stoffwechsel. *Hoppe-Seylers Zeitschdft für physiologische Chemie*. 1929, vol. 181, p. 42-53. At the same time, in later papers other authors ascertained that y-butyrobetaine is extremely low toxic (LD50>7000 mg/kg, s.c.) ROTZSCH, W. Iber die Toxizitat des Carnitins und einiger verwandter Stoffe. *Acta biol. med. germ*. 1959, vol. 3, p. 28-36.

In the literature data on nonsubstututed γ-butyrobetaine cardiovascular effects are missed, thought it was reported HOSEIN, E. A. Pharmacological actions of γ-butyrobetaine. *Nature*. 1959, vol. 183, p. 328-329. that γ-butyrobetaine is a substance similar to acetyl choline with a prolonged action. However, later the same authors reported that by an error the experiments involved, instead of γ-butyrobetaine, its methyl esther which in fact possesses cholinergic properties. Contrary to the former γ-butyrobetaine was characterised as a pharmacologically inert substance HOSEIN, E. A. Isolation and probable functions of betaine esters in brain metabolism. *Nature*. 1960, vol. 187, p. 321-322.

As structurally related compounds to 4-[ethyl(dimethyl) ammonio] butanoate are disclosed in:

GB 1238868 A 14 Jul. 1971 were disclosed betaines, such as 4-trimethylammoniobutanoate, used for polymers. Howerver no pharmacological propeties of these betaines weren't presented;

U.S. Pat. No. 5,973,026 A (XEROX CORP) 26 Oct. 1999 were disclosed 4-trimethylammoniobutanoate and 3-[diethyl(methyl)ammonio]propionate for using for ink compositions;

LLOYD ANDREW, et al. A comparison of glycine, sarcosine, N,N-dimethylglycine, glycinebetaine and N-modified betaines as liposome cryoprotectants. *Journal of pharmacy and pharmacology*. 1992, vol. 44, no. 6, p. 507-511 disclosed 2-[ethyl(dimethyl)ammonio]acetate used as cryoprotectants for liposomes;

DAVID B., THOMAS, et al. Synthesis, Characterization, and Aqueous Solution Behavior of Electrolyte- and pH-Responsive Carboxybetaine-Containing Cyclocopolymers. *Macromolecules*. 2003, vol. 36, no. 26, p. 9710-9715 disclose 4-[diallyl(methyl)ammonio]butanoate and its synthesis starting from N,N-diallyl-N-methylaminiom and ethyl 4-bromobutanoate. The free acis is obtained from the ester in a second step using Amberlite ion exchange resin. The product is used as intermediate to synthesise polymers;

*Prelog V* 1930, vol. 2, p. 712-722 disclosed the synthesis of 4-trimethylammoniobutanoate starting from 4-dimethylammoniobutanoate and methyliodide;

4-Trimethylammoniobutanoate and its synthesis starting from trimethylamine and ethyl 4-bromobutanoate was described JP 2009096766 A (KONAN GAKUEN) 7 May 2009. The free acid is obtained from the ester in a second step using Amberlite ion exchange resin;

WO 2008/055843 A (KALVINSH IVARS; CHERNOBROVIJS ALEKSANDRS; VARACHEVA LARISA; PUGOVICHS OSVALDS) 15 May 2008 was described 4-trimethylammoniobutanoate and synthesis, which started from the correspondin ester and using KOH-solution;

CA 2508094 A (VIVIER CANADA INC) 20 Nov. 2006 was disclosed betaines, such as 4-trimethylammoniobutanoate, for use as medicament for accelerating collagen synthesis;

U.S. Pat. No. 5,965,615 A (TAIHO PHARMACEUTICAL CO LTD; VALSTS ZINATNISKA IESTADE BEZP) 12 Oct. 1999 was disclosed 4-trimethylammoniobutanoate as a medicament for the treatment of myocardial metabolic disorder, the same compound was disclosed in US 2007191381 A (CONCERT PHARMACEUTICALS INC) 16 Aug. 2007 for treatment of myocardial infarction.

3- (2,2,2-Trimethylhydrazinium) propionate dihydrate is known as compound with cardioprotective properties (this substance being known under its International Nonproprietary Name of Meldonium). 3- (2,2,2-Trimethylhydrazinium) propionate is disclosed in U.S. Pat. No. 4,481,218

(INST ORGANICHESKOGO SINTEZA) 6 Nov. 1984 as well in U.S. Pat. No. 4,451,485 A (INSTITU ORCH SINTEZA AKADEMII) 29 May 1984.

It is well known that 3-(2,2,2-trimethylhydrazinium) propionate as dihydrate is widely used for controlling carnitine and gamma-butyrobetaine concentration ratio and consequently the speed of fatty acid beta-oxidation in the body DAMBROVA M., LIEPINSH E., KALVINSH I. I. Mildronate: cardioprotective action through carnitine-lowering effect. *Trends in Cardiovascular Medicine,*. 2002, vol. 12, no. 6, p. 275-279.

Due to these properties, Meldonium is extensively applied in medicine as an anti-ischemic, stress-protective and cardioprotective drug in treating various cardio- vascular diseases and other pathologies involving tissue ischemia KARPOV R. S., KOSHELSKAYA O. A., VRUBLEVSKY A. V., SOKOLOV A. A., TEPLYAKOV A. T., SKARDA I., DZERVE V., KLINTSARE D., VITOLS A., KALNINS U., KALVINSH I., MATVEYA L., URBANE D. Clinical Efficacy and Safety of Mildronate in Patients With Ischemic Heart Disease and Chronic Heart Failure. *Kardiologiya.* 2000, no. 6, p. 69-74. In the treatment of cardiovascular diseases the mechanism of action of 3-(2,2,2-trimethylhydrazinium)propionate based on limitation of carnitine biosynthesis rate and related long-chain fatty acid transport limitation through mitochondria membranes SIMKHOVICH B. Z., SHUTENKO Z. V., MEIRENA D. V., KHAGI K. B., MEZHAPUKE R. J., MOLODCHINA T. N., KALVINS I. J., LUKEVICS E.

3-(2,2,2,-Trimethylhydrazinium)propionate (THP)—a novel gamma-butyrobetaine hydroxylase inhibitor with cardioprotective properties. *Biochemical Pharmacology.* 1988, vol. 37, p. 195-202., KIRIMOTO T., ASAKA N., NAKANO M., TAJIMA K., MIYAKE H., MATSUURA N. Beneficial effects of MET-88, a γ-butyrobetaine hydroxylase inhibitor in rats with heart failure following myocardial infarction. *European Journal of Pharmacology.* 2000, vol. 395, no. 3, p. 217-224.

SUMMARY OF INVENTION

As it was known what Meldonium dihydrate has cardioprotective effect; however there are no data that y-butyrobetaine itself has pronounced cardioprotective effect. In the patent EP 0845986 B (KALVINSH IVARS, VEVERIS MARIS) 2 Apr. 2003 is disclosed pharmaceutical composition of Meldonium dihydrate and γ-butyrobetaine for use in the treatment of cardiovascular diseases.

An object of the present invention is to provide a compound, which has pronounced cardioprotective effect.

The above-mentioned object is attained by providing new compound 4-[ethyl(dimethyl)ammonio]butanoate (compound of formula 5), which has similar structure to Meldonium or γ-butyrobetaine.

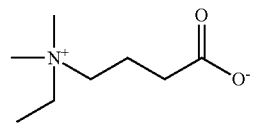

To our surprise, 4-[ethyl(dimethyl)ammonio]butanoate posses pronounced cardioprotective effect and are more effective as Meldonium dihydrate in vivo myocardial infarction models, due this properties 4-[ethyl(dimethyl)ammonio] butanoate may be used in medicine. 4-[ethyl(dimethyl)ammonio]butanoate can be use as a solution of injection and as tablets.

The following object of the present invention is a method of preparation of said compound of formula 5.

There are disclosed four processes, which can be used in purpose to prepare target compound 4-[ethyl(dimethyl)ammonio] butanoate of formula 5, see scheme bellow.

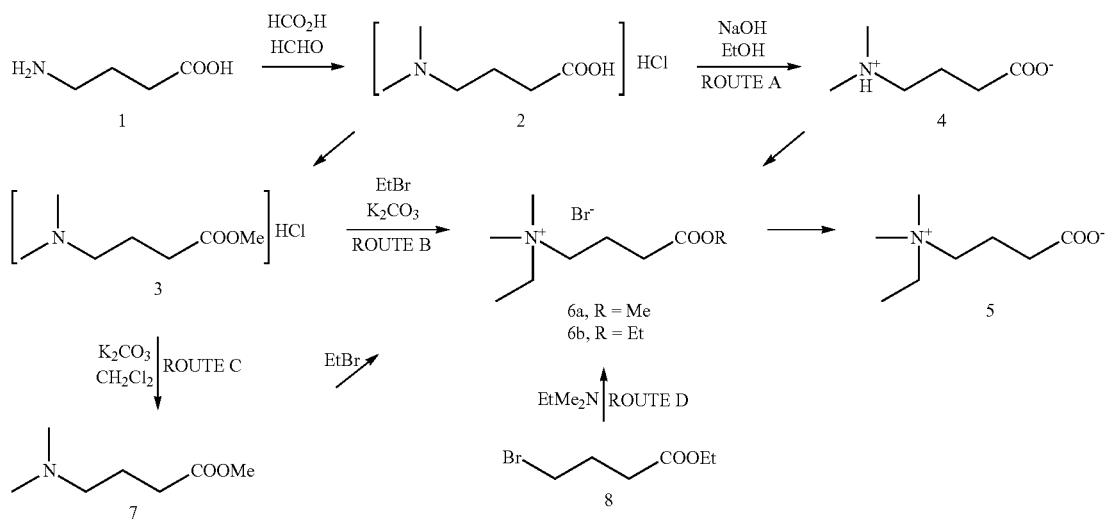

First process (Route A) involves following process steps:

a) adding ethyl bromide to 4-(dimethylammonio)butanoate to produce N-ethyl-4-methoxy-N,N-dimethyl-4-oxo-1-butanaminium bromide;

b) treat N-ethyl-4-methoxy-N,N-dimethyl-4-oxo-1-butanaminium bromide with potassium hydroxide to obtain desired compound 4-[ethyl(dimethyl)ammonio] butanoate.

Second process (Route B) involves following process steps:

a) adding potassium carbonate and bromethane to 4-methoxy-N,N-dimethyl-4-oxo-1-butanaminium chloride to produce N-ethyl-4-methoxy-N,N-dimethyl-4-oxo-1-butanaminium bromide;
b) pass N-ethyl-4-methoxy-N,N-dimethyl-4-oxo-1-butanaminium bromide thourgh ion exchange resin column to obtain 4-[ethyl(dimethyl)ammonio] butanoate .

Third process (Route C) involves following process steps:
a) adding potassium carbonate and dichloromethane to 4-methoxy-N,N-dimethyl-4-oxo-1-butanaminium chloride to produce methyl-4-(dimethylamino)butanoate;
b) stir methyl-4-(dimethylamino)butanoate with bromoethane in dichloromethane to obtain N-ethyl-4-methoxy-N,N-dimethyl-4-oxo-1-butanaminium bromide;
c) treat N-ethyl-4-methoxy-N,N-dimethyl-4-oxo-1-butanaminium bromide with potassium hydroxide to obtain desired compound 4-[ethyl(dimethyl)ammonio]butanoate.

Fourth process (Route D) involves following process steps:
a) add N,N-dimethylethylamine to ethyl 4-bromobutanoate in dichloromethane to obtain 4-ethoxy-N-ethyl-N,N-dimethyl-4-oxo-1-butanaminium bromide;
b) pass 4-ethoxy-N-ethyl-N,N-dimethyl-4-oxo-1-butanaminium bromide thourgh ion exchange resin column to obtain 4-[ethyl(dimethyl)ammonio] butanoate.

DESCRIPTION OF EMBODIMENTS

The present invention will be described in more detail by referring to the following non-limiting examples.

Synthesis of 4-[Ethyl(Dimethyl)Ammonio]Butanoate (5)

Preparation of 4-methoxy-N,N-dimethyl-4-oxo-1-butanaminium chloride (3)

To a solution of 3-carboxy-N,N-dimethyl-1-propanaminium chloride (2) (45.93 g, 0.27 mol) in anh. methanol (300 ml) at (−10)-0° C. slowly thionyl chloride (55 ml, 0.76 mol) was added and the reaction mixture was stirred for an hour at ambient temperature. The reaction mixture thereafter was stirred at 40-50° C. for 3 hours and evaporated. The residue was dissolved in acetone (110 ml) and precipitated by adding ether (400 ml). The solid was filtered, washed with ether, and once more dissolved in acetone (110 ml) followed by the precipitation with ether (400 ml). The precipitate was filtered, washed with ether, and dried to give 38.4 g (77%) of 4-methoxy-N,N-dimethyl-4-oxo-1-butanaminium chloride.
$^1$H NMR (DMSO-d$_6$, HMDSO) δ: 1.91 (qui, J=7.7 Hz, 2H); 2.43 (t, J=7.74 Hz, 2H); 2.71 (d, J=4.9 Hz, 6H); 2.98-3.06 (m, 2H), 3.61 (s, 3H); 10.76 (b s, 1H).

Route A

Preparation of 4-[ethyl(dimethyl)ammonio]butanoate (5)

A mixture of 4-(dimethylammonio)butanoate (4) (7.87 g, 0.06 mol) and ethyl bromide (13.08 g, 0.12 mol) in anhydrous acetone (20 ml) was refluxed until the starting material 4-(dimethylammonio)butanoate disappeared (TLC control, methanol-aquous ammonium hydroxide, 3:1)). The reaction mixture was supplemented with isopropanol (100 ml) and the solution was evaporated to dryness. A solution of solution of KOH (7.28 g, 0.13 mol) in 96% ethanol (70 ml) was added to the residue at 0° C. and reaction mixture was stirred for 4 hours. The precipitate was filtered off and the filtrate was treated with 2 N HCl in methanol until the pH of the medium was 7-8. The reaction mixture was kept at −18° C. for 12 hours and was filtered. The filtrate was evaporated to dryness and the residue was azeotropically dried with isopropanol (3×100 ml). The obtained oily solid (13.4 g) was dissolved in isopropanol (100 ml) and was kept at −18° C. for 12 hours. The precipitate was filtered and the filtrate was evaporated to dryness and crystallized from acetone (30 ml) at −18° C. to give 4.14 g (43%) of 4-[ethyl(dimethyl)ammonio]butanoate.
$^1$H NMR (DMSO-d6, HMDSO) δ: 1.24 (t, J=7.3 Hz, 3H); 1.68-1.78 (m, 2H); 1.87 (t, J=6.5 Hz, 2H); 2.96 (s, 6H); 3.16-3.23 (m, 2H); 3.29 (q, J=7.3 Hz, 2H). LC ESI-MS (m/z): 160 [M+H]$^+$.
Anal. Calculation for $C_8H_{17}NO_2 \cdot 1.3$ $H_2O$: C, 52.61, H, 10.82, N7.67. Found: C, 52.64, H, 11.00, N, 7.58

Route B

Preparation of N-ethyl-4-methoxy-N,N-dimethyl-4-oxo-1-butanaminium bromide (6a)

A mixture of 4-methoxy-N,N-dimethyl-4-oxo-1-butanaminium chloride (3) (7.27 g, 0.04 mol), anhydrous $K_2CO_3$ (5.52 g, 0.04 mol), and bromoethane (4.48 ml, 0.06 mol) in acetone (40 ml) was vigorously stirred at ambient temperature for 2 days. The precipitate was filtered, washed with acetone, suspended in isopropanol (100 ml), and vigorously stirred at ambient temperature for 2 hours. The mixture was filtered, the filtrate was evaporated to dryness and azeotropically dried several times with isopropanol. The residue was crystallized from acetone (10 ml) by adding ethyl acetate (35 ml) and dried over $P_2O_5$ in vacuo to afford 6.51 g (64%) of Nethyl-4-methoxy-N,N-dimethyl-4-oxo-1-butanaminium bromide.
$^1$H NMR (CDCl$_3$, HMDSO) δ: 1.44 (t, J=7.2 Hz, 3H); 2.01-2.12 (m, 2H); 2.55 (t, J=6.6 Hz, 2H); 3.40 (s, 6H); 3.66-3.73 (m, 4H); 3.69 (s, 3H).
LC ESI-MS (m/z): 174 [M+H]$^+$.
Anal. Calcd for $C_9H_{20}BrNO_2 \cdot 0.09$ $H_2O$: C, 42.26, H, 7.95, N, 5.48. Found: C, 42.26, H, 8.28, N, 5.35.

Preparation of 4-[ethyl(dimethyl)ammonio]butanoate (5)

A solution of N-ethyl-4-methoxy-N,N-dimethyl-4-oxo-1-butanaminium bromide (6a) (6.51 g, 0.025 mol) in ethanol (20 ml) was passed through Amberlite® IRA-410 (OH) ion exchange resin column (190 ml) slowly eluting with ethanol (100 ml). The eluate was evaporated to dryness and the residue was several times azeotropically dried with isopropanol, then dissolved in isopropanol (50 ml) and kept at 0° C. for 12 hours. The mixture was filtered and the filtrate was evaporated. The residue (7.35 g) was mixed with cold ethyl acetate and kept at 0° C. for 12 hours. The mixture was filtered and the precipitate was dried over $P_2O_5$ in vacuo to furnish 3.54 g (86%) of 4-[ethyl(dimethyl)ammonio]butanoate. The purity of the material was increased by passing a water solution of 4-[ethyl(dimethyl)ammonio] butanoate through DOWEX® 50WX8 ion exchange resin. The solution was evaporated to dryness; the residue was azeotropically dried with isopropanol followed by drying in vacuo over $P_2O_5$ to give 1.27 g (31%) of 4-[ethyl(dimethyl)ammonio]butanoate.

Route C

Preparation methyl 4-(dimethylamino)butanoate (7)

A suspension of 4-methoxy-N,N-dimethyl-4-oxo-1-butanaminium chloride (3) (5.44 g, 0.03 mol) and anhydrous $K_2CO_3$ (5.52 g, 0.04 mol) in dichloromethane (70 ml) was vigorously stirred at ambient temperature for 24 hours. The precipitate was filtered, washed with dichloromethane, and the filtrate was evaporated. The residue was distilled at 32-35° C./3-4 mm Hg to give 2.88 g (66%) of 4-(dimethylamino) butanoate.

$^1$H NMR (DMSO-$d_6$, HMDSO) δ: 1.64 (qui, J=7.2 Hz, 2H); 2.09 (s, 6H); 2.17 (t, J=7.1 Hz, 2H); 2.30 (t, J=7.4 Hz, 2H); 3.57 (s, 3H).

Preparation of N-ethyl-4-methoxy-N,N-dimethyl-4-oxo-1-butanaminium bromide (6a)

A mixture of methyl 4-(dimethylamino)butanoate (7) (1.45 g, 10 mmol) and bromoethane (1.2 ml, 16 mmol) in dichloromethane (15 ml) was stirred at ambient temperature. The reaction mixture was evaporated to dryness, the white solid (2.438 g) was triturated with acetone, filtered and dried in vacuo over P2O5 to afford 2.397 g (94%) of N-ethyl-4-methoxy-N,N-dimethyl-4-oxo-1-butanaminium bromide.

Route D

Preparation
4-ethoxy-Nethyl-N,N-dimethyl-4-oxo-1-butanaminium bromide (6b)

To a solution of ethyl 4-bromobutanoate (8) (19.5 g, 0.1 mol) in dichloromethane at ice bath temperature N,N-dimethylethylamine (10.8 ml, 0.1 mol) was added and stirred at ambient temperature overnight. The reaction mixture was evaporated to dryness, the residue was triturated with acetone (50 ml) and kept at 0° C. for 0.5 hours. The precipitate was filtered and dried in vacuo over $P_2O_5$ to afford 22.274 g (94%) of 4-ethoxy-N-ethyl-n,N-dimethyl-4-oxo-1-butanaminium bromide.

$^1$H NMR (CDCl$_3$, HMDSO) δ: 1.26 (t, J=7.2 Hz, 3H); 1.44 (t, J=7.4 Hz, 3H); 2.00-2.11 (m, 2H); 2.52 (t, J=6.6 Hz, 2H); 3.40 (s, 6H); 3.64-3.73 (m, 2H); 3.69 (q, J=7.4 Hz, 2H); 4.14 (q, J=7.2 Hz, 2H).

Preparation of 4-[ethyl(dimethyl)ammonio]butanoate (5)

A solution of 4-ethoxy-N-ethyl-N,N-dimethyl-4-oxo-1-butanaminium bromide (6b) (12.00 g, 44:7 mmol) in water (10 ml) was passed through Amberlite® IRA-410 (OH) ion exchange resin column (250 ml) eluting slowly (ca. 10 drops/min) with ethanol (TLC control). The eluate was evaporated and the residue (12 g) was dissolved in water (50 ml). To this solution DOWEX® 50WX8 ion exchange resin (5 g) was added and stirred at ambient temperature for 0.5 hours. The reaction mixture was filtered through celite (1 cm) and the eluate was evaporated to dryness. The residue was azeotropically dried with isopropanol, acetonitrile, and acetone. The obtained solid was triturated with acetone (10 ml) and the mixture was kept at 0° C. for 2 h. The precipitate was filtered and dried in vacuo over P205 to give 4.65 g (65%) of 4-[ethyl (dimethyl)ammonio]butanoate.

$^1$H NMR (DMSO-$d_6$, HMDSO) δ: 1.24 (t, J=7.3 Hz, 3H); 1.66-1.76 (m, 2H); 1.81 (t, J=6.4 Hz, 2H); 2.95 (s, 6H); 3.16-3.23 (m, 2H); 3.29 (q, J=7.3 Hz, 2H). LC ESI-MS (m/z): 160 [M+H]$^+$.

Anal. Calcd for $C_8H_{17}NO_2$·1.55 $H_2O$: C, 51.34; H, 10.82; N, 7.48. Found: C, 51.36, H, 11.40, N, 7.34.

Cardioprotective Activity

Fifty male, 10 weeks old Wistar rats weighing 200-250 g were housed under standard conditions (21-23° C., 12 h light-dark cycle) with unlimited access to food (R3 diet, Lactamin AB, Sweden) and water.

Rats were adapted to local conditions for two weeks before the start of treatment. Meldonium dihydrate at a dose of 5 mg/kg or 100 mg/kg, gamma-butyrobetaine at a dose of 5 mg/kg and EG at doses of 20mg/kg were administered p.o. daily for 8 weeks. Control rats received water.

Isolated Rat Heart Infarction Study

The isolated rat heart experiment was performed essentially as described earlier (Liepinsh et al., J. Cardiovasc. Pharmacol. 2006; 48(6):314-9). Twenty-four hours after the last drug administration hearts were excised and retrogradely perfused via the aorta at a constant pressure with oxygenated Krebs-Henseleit buffer at 37° C. The heart rate, left ventricle end-diastolic pressure and left ventricle developed pressure were continuously recorded. Coronary flow was measured using an ultrasound flow detector (HSE) and the PowerLab 8/30 system from ADInstruments. The hearts were perfused for 20 min to stabilize the hemodynamic functions and then occlusion was performed for 60 min by constricting threads through a plastic tube. Successful occlusion was confirmed by a coronary flow decrease of about 40 percent. Reperfusion was achieved by releasing the threads. At the end of the 150-min reperfusion period, the risk zone was delineated with 0.1% methylene blue. The hearts were then sectioned transversely from the apex to the base in five slices 2 mm in thickness and incubated in 1% triphenyltetrazolium chloride in phosphate buffer (pH 7.4, 37° C.) for 10 min to stain viable tissue red and necrotic tissue white. Computerized planemetric analysis of Sony A900 photographs was performed using Image-Pro Plus 6.3 software to determine the area at risk and area of necrosis expressed as a % of the left ventricle. The obtained values were then used to calculate the infarct size (IS) as a % of risk area according to the formula:

Infarct Size=Area of Necrosis/Area at Risk×100%.

Effects in Isolated Rat Heart Infarction Model

The anti-infarction effect of examined substances was investigated in an isolated rat heart infarction model. During occlusion of left coronary artery, the coronary flow in all experimental groups was decreased for 40% (from 11 ml/min to 7 ml/min). Moreover, the drop of developed left ventricular pressure for 50% was observed. The heart rate during the occlusion period did not change significantly. In reperfusion stage, coronary flow, developed left ventricular pressure, ±dp/dt values were recovered till about 80% of control level. There were no significant differences between control and treatment groups.

Effects of Meldonium dihydrate (5 mg/kg un 100 mg/kg), gamma-butyrobetaine (5 mg/kg) and 4-[ethyl(dimethyl)ammonio]butanoate (EG) (5 mg/kg) after 2 weeks of treatment on infarct size in the isolated rat heart infarction experiment are presented in Table 1.

TABLE 1

Effects of Meldonium dihydrate, gamma-butyrobetaine and EG on infarct size

| | Infarct size, % of control |
|---|---|
| Control | 100.0 ± 5 |
| Meldonium dihydrate 5 mg/kg | 95 ± 9 |
| Meldonium dihydrate 100 mg/kg | 76 ± 10* |
| Gamma-butyrobetaine 5 mg/kg | 90 ± 5 |
| EG 5 mg/kg | 59 ± 6* |

Each value represents the mean ± s.e.m. of 9-10 animals.
*Significantly different from control group (t-test P < 0.05), As it is presented in Table 1, Meldonium dihydrate treatment at a dose of 5 mg/kg decreased the infarct size by 5%, therapeutical activity of Meldonium dihydrate was observed only at 100 mg/kg, when infarct size was decreased the by 24%. Gamma-butyrobetaine at a dose of 5 mg/kg had no therapeurical effect. 4-[ethyl(dimethyl)ammonio]butanoate at dose of 5 mg/kg observed the best threpeutical effect decreasing infarct size by 41%.

The invention claimed is:

1. A process for preparing 4-[ethyl(dimethy)ammonio]butanoate comprising:
   a) adding ethyl bromide to 4-(dimethylammonio)butanoate in acetone to produce N-ethyl-4-methoxy-N,N-dimethly-4-oxo-1-butanaminium bromide and
   b) treating N-ethyl-4-methoxy-N,N-dimethyl-4-oxo-1-butanaminium bromide with a solution of potassium hydroxide in ethanol to obtain 4-[ethyl(dimethyl)ammonio] butanoate.

2. A process for preparing 4-[ethyl(dimethyl)ammonio] butanoate comprising:
   a) adding potassium carbonate and bromoethane to 4-methoxy-N, N-dimethyl-4-oxo-1-butanaminium chloride in acetone to produce N-ethyl-4-methoxy-N, N-dimethyl-4-oxo-1-butanaminium bromide and
   b) passing N-ethyl-4-methoxy-N, N-dimethyl-4-oxo-1-butanaminium bromide in the presence of ethanol through an ion exchange resin column to obtain 4-[ethyl (dimethyl)ammonio] butanoate.

3. A process for preparing 4-[ethyl(dimethyl)ammonio] butanoate comprising:
   a) adding potassium carbonate and dichloromethane to 4-methoxy-N,N-dimethyl-4-oxo-1-butanaminium chloride to produce methyl-4-(dimethylamino)butanoate;
   b) stirring methyl-4-(dimethylamino)butanoate with bromoethane in dichloromethane to obtain N-ethyl-4-methoxy-N,N-dimethyl-4-oxo-1-butanaminium bromide; and
   c) treating N-ethyl-4-methoxy-N,N-dimethlyl-4-oxo-1-butanaminium bromide with solution of potassium hydroxide in ethanol to obtain 4-[ethyl(dimethy)ammonio] butanoate.

4. A process for preparing 4-[ethyl(dimethyl)ammonio] butanoate comprising:
   a) adding N,N-dimethylethylamine to ethyl 4-bromobutanoate in dichioromethane to obtain 4-ethoxy-ethyl-N,N-dimethyl-4-oxo-1-butanaminium bromide and
   b) passing 4-ethoxy-N-ethyl-N, N-dimethyl-4-oxo-1-butanaminium bromide dissolved in water through an on exchange resin column to obtain 4-[ethyl(dimethyl)ammoniol] butanoate.

* * * * *